United States Patent
Passaniti et al.

(10) Patent No.: US 11,378,537 B2
(45) Date of Patent: Jul. 5, 2022

(54) METHOD OF POWERING SENSORS, CORRESPONDING CIRCUIT AND DEVICE

(71) Applicant: STMicroelectronics S.r.l., Agrate Brianza (IT)

(72) Inventors: Fabio Passaniti, Syracuse (IT); Enrico Rosario Alessi, Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 834 days.

(21) Appl. No.: 16/256,041

(22) Filed: Jan. 24, 2019

(65) Prior Publication Data

US 2019/0242844 A1   Aug. 8, 2019

(30) Foreign Application Priority Data

Feb. 5, 2018   (IT) .................. 102018000002405

(51) Int. Cl.
*G01N 27/16* (2006.01)
*G01N 27/14* (2006.01)
*G01N 27/12* (2006.01)
*G06F 1/3203* (2019.01)
*G01N 33/00* (2006.01)

(52) U.S. Cl.
CPC ........... *G01N 27/14* (2013.01); *G01N 27/124* (2013.01); *G01N 27/128* (2013.01); *G01N 33/0047* (2013.01); *G06F 1/3203* (2013.01)

(58) Field of Classification Search
CPC ...... G01N 27/00; G01N 27/12; G01N 27/124; G01N 27/128; G01N 27/14; G01N 27/16; G01N 27/407; G01N 33/00; G01N 33/0047; G06F 1/3203
See application file for complete search history.

(56) References Cited

U.S. PATENT DOCUMENTS

| | | | | |
|---|---|---|---|---|
| 5,142,898 A | * | 9/1992 | Kauschke | G01N 27/16 73/23.31 |
| 6,888,467 B2 | * | 5/2005 | Green | G08B 21/16 73/23.31 |
| 2008/0034841 A1 | | 2/2008 | Bahs et al. | |
| 2016/0077031 A1 | | 3/2016 | Lechner et al. | |

(Continued)

FOREIGN PATENT DOCUMENTS

| | | |
|---|---|---|
| DE | 102007057519 A1 | 10/2009 |
| JP | S6039542 A | 3/1985 |

OTHER PUBLICATIONS

Rossi, Maurizio, et al., "Analyzing the Transient Response of MOX Gas Sensors to Improve the Lifetime of Distributed Sensing Systems", Advances in Sensors and Interfaces (IWASI), 5th IEEE International Workshop, 2013, 6 pages.

(Continued)

*Primary Examiner* — Nguyen Q. Ha
(74) *Attorney, Agent, or Firm* — Slater Matsil, LLP (57) ABSTRACT

A method of reducing power consumption in portable devices includes providing a sensor producing a sensing signal indicative of sensed entity and powering the sensor. Powering the sensor includes providing a first power value for a first time interval, providing a second power value for a second time interval, the second power value being different from the first power value, and discontinuing powering for a third time interval.

20 Claims, 8 Drawing Sheets

(56) References Cited

U.S. PATENT DOCUMENTS

2016/0216227 A1   7/2016  Boni
2020/0209176 A1*  7/2020  Brueser .................. G01N 27/14

OTHER PUBLICATIONS

Kato, Yo, et al., "Temperature-dependent dynamic response enables the qualification and quantification of gases by a single sensor", Sensors and Actuators B, vol. 40, No. 1, May 1997, pp. 33-37.
Burresi, A., et al., "33.2: SnO2 Sensors with Variable Operating Temperature for CO Detection: Selectivity Enhancement", Proceedings of IEEE Sensors, Jun. 12, 2001, pp. 361-365.

* cited by examiner

METHOD OF POWERING SENSORS, CORRESPONDING CIRCUIT AND DEVICE

CROSS-REFERENCE TO RELATED APPLICATIONS

This application claims priority to Italian Patent Application No. 102018000002405, filed on Feb. 5, 2018, which application is hereby incorporated herein by reference.

TECHNICAL FIELD

Embodiments of the invention relate to a method of powering sensors and a corresponding circuit and device.

BACKGROUND

Gas sensors based on metal oxide semiconductors (MOX) are conventionally applied to detection of target gases.

Ideally, a MOX sensing element should be maintained active at a preferred working temperature predefined for a specific target gas and application. However, micro-hot plates MHP, which provide heat to the sensing elements, may be responsible for significant power consumption.

In case of wearable and portable devices, limitations to such power consumption may be desirable.

Intermitted heating of the micro-hot plate represents a conventional approach used for reducing the power consumption of the gas sensors: a micro-hot plate may be alternatively powered, by a pulse switching on and off over time, i.e., a pulse switching between a high and a low value. However, a trade-off between level power consumption and performances (e.g., accuracy, sensitivity and stability) may be set for avoiding degradation of the gas sensor, e.g., by reducing the duty cycle and/or the current level.

SUMMARY

The description relates to methods of reducing power consumption of sensing elements, e.g., MOX metal oxide semiconductor based gas sensors used for detection of a target gas, e.g., volatile organic compounds (VOC), nitrogen-based compounds (e.g., ammonia or nitrogen oxides) and/or elemental gases (such as oxygen or hydrogen) detection.

One or more embodiments may relate to a gas module arranged on portable low-power devices such as mobile phones, handled devices or wearable devices, which may be used for air quality detection in closed environments such as homes or vehicles.

One or more embodiments may be applied to the field of environmental sensors in the consumer, automotive, industrial and medical markets.

Various embodiments may provide improved solutions to drawbacks of known solutions. An object of one or more embodiments is to facilitate reducing power consumption in a gas sensing element, without degrading performance of the sensor.

According to one or more embodiments, such an object may be achieved by means of a method as described herein. One or more embodiments may include a corresponding circuit and a corresponding device (e.g., a portable device or a vehicle comprising one or more gas sensors and a circuit according to one or more embodiments).

One or more embodiments may relate to reducing a pulse duration during intermitted heating. The sensor response values, collected when the reduced pulse is active (i.e., the gas sensor is powered on), may be used for predicting the sensor response values in a time interval that occurs between the end of the reduced pulse (i.e., when the gas sensor is switched off) and the end of the conventional pulse (i.e., when the gas sensor would be conventionally switched off).

One or more embodiments may predict the sensor response, e.g., a resistance, values via a characterization model, e.g., gas sensor MOX resistance characterization models that may be specific for each MOX-based gas sensor (e.g., WO3 base, SnO2, PdSnO2, ZnO2, etc.).

Accordingly, in one or more embodiments, the micro-hot plate comprised in the sensors may be powered on during the reduced pulse duration and may remain switched off during the time interval between the end of the reduced pulse and the end of the conventional pulse.

BRIEF DESCRIPTION OF THE DRAWINGS

One or more embodiments will now be described, by way of example only, with reference to the annexed figures, wherein.

DETAILED DESCRIPTION OF ILLUSTRATIVE EMBODIMENTS

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

Figure 1A:
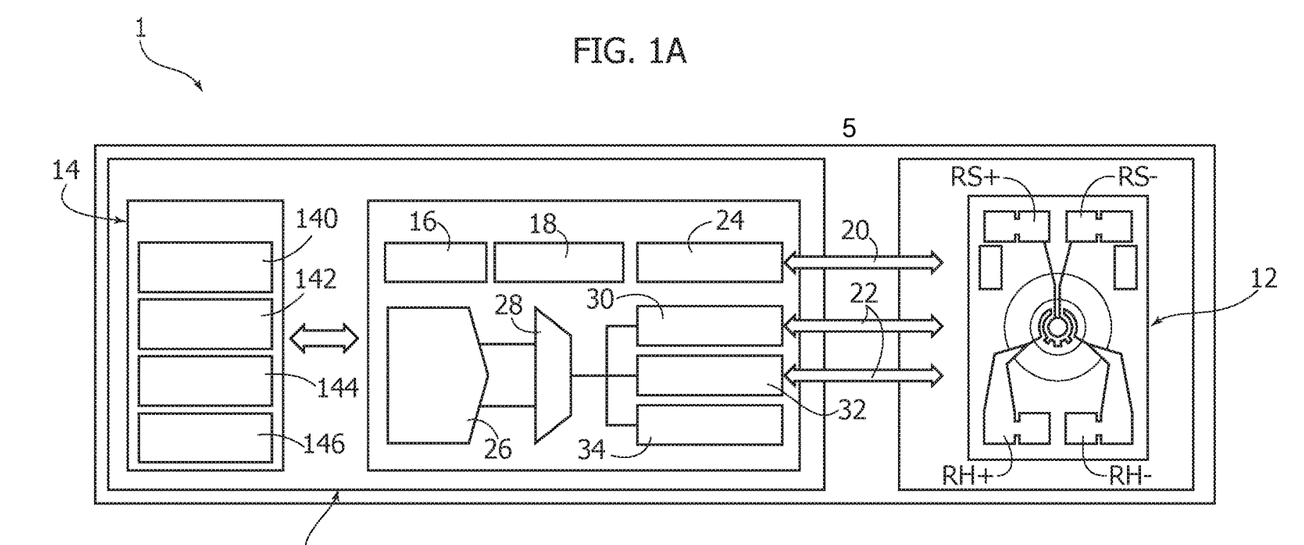
FIGS. 1A and 1B represent an example of a device and a sensor, respectively, according to one or more embodiments.

FIG. 1A represents an example of a portable device 1 according to one or more embodiments, comprising an (e.g., application-specific) integrated circuit 10 and one or more sensors 12 enclosed in a common package 5. The integrated circuit 10 is coupled to the sensor(s) 12 and may be configured to perform the steps of the method according to one or more embodiments. The circuit according to one or more embodiments may comprise a processor circuit 14 suited to be coupled to power nodes 20 and input/output nodes 22, and which can be configured to supply power to the sensor(s) 12 (via nodes 20) and to sense (via nodes 22) signals indicative of an event produced by the sensor(s) 12, e.g., for receiving the sensing data therefrom. Corresponding terminals may be found in the sensor(s) 12: e.g., power terminals RH+, RH− and sensing terminals RS+, RS− to be connected to the power nodes 20 and input nodes 22 of the circuit according to one or more embodiments.

FIG. 1A shows various other elements which, in one or more embodiments, may be included in the circuit 10. For instance the processor circuit 14 may comprise a digital front-end, e.g., comprising a phase generator from the analog front-end 140, one or more memories 142, one or more digital filters 144 and one or more I2C/SPI interfaces 146.

In one or more embodiments, the circuit 10 may comprise further elements involved in operating the sensor(s) 12. The following designations may apply to the blocks comprised in the circuit as illustrated in FIG. 1A:
- 16: clock;
- 18: reference current/voltage generator;
- 24: heater current driver;
- 26: analog-to-digital converter;
- 28: multiplexer;
- 30: heater analog front-end, AFE;
- 32: sense analog front-end, AFE; and
- 34: heater and humidity H/T sensor.

The heater and humidity H/T sensor can be arranged in an opposite position of the device 1 with respect to the sensor 12, in order to facilitate avoiding interferences therewith.

Figure 1B:
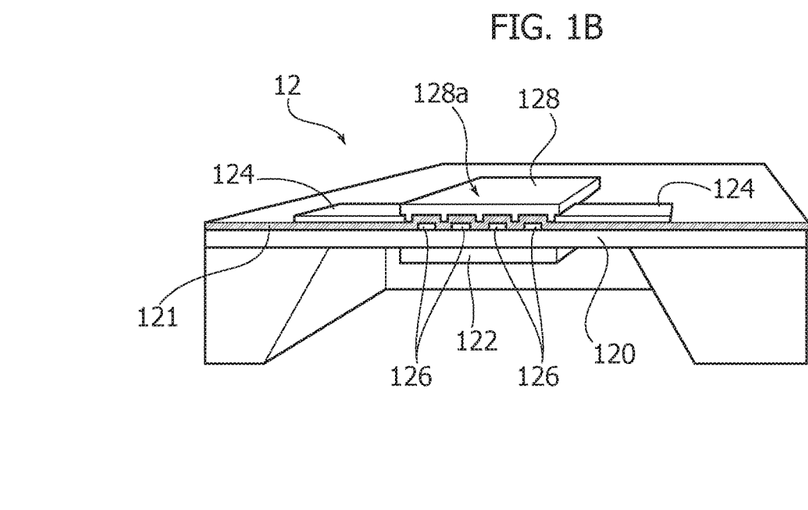

FIG. 1B represents a possible implementation a sensor 12, e.g., comprising one or more gas sensing elements in MOX—metal oxide—technology. The sensor 12 may comprise a micro-hot plate MHP, comprising a membrane 120, an electrical insulating layer 121, one or more heaters 126 and a layer of metal oxide sensing material 128, a silicon substrate 122, and two electrodes 124, arranged substantially sidewise of the layer of metal oxide sensing material 128, e.g., on opposite lateral sides thereof.

In one or more embodiments, the micro-hot plate MHP may comprise the membrane 120, e.g., suspended, in order to facilitate good thermal dissipation and isolation, which may have ventilation holes thereon to avoid stitching issues during assay. The membrane 120 may comprise one or more heater elements 126 (e.g., platinum resistances) arranged thereon. Also, the micro-hot plate may comprise a layer of MOX sensing material 128 (e.g., tin dioxide—SnO2), which may be arranged over the heater element(s) 126.

For example, as exemplified in FIG. 1B, a layer of electrical insulating material 121 may be provided between the heater(s) 126 plus membrane 120 and the layer of MOX sensing material 128, which may be provided onto the electrical insulating layer 121 by means of specific techniques, for example micro-dispensing or screen printing. Accordingly, the heater(s) 126 may be sandwiched between the electrical insulating layer 121 and the membrane 120.

In one or more embodiments, the layer of MOX sensing material 128 may have a front surface 128a, opposite to a surface of the layer of MOX sensing material 128 facing towards the heater(s) 126, which may be exposed to air and may sense a target gas, e.g., a volatile organic compound VOC, if present.

In one or more embodiments, the two electrodes 124 may be placed onto the electrical insulating layer 121, at opposite lateral surfaces of the layer of MOX sensing oxide 128, with the two electrodes 124 electrically connected to the layer of MOX sensing material 128.

Thus, the heater(s) 126 arranged below the layer of MOX sensing material 128 may allow to heat the layer of MOX sensing material 128 to one or more preferred working temperature values, for example between 350-400° C., and to maintain such values during operation of the sensor 12. The layer of MOX sensing material 128 may be heated in order to be reactive and sensitive to the presence of a target gas. e.g., a volatile organic compound VOC such as ethanol, toluene, benzene, formaldehyde.

Gas sensors 12, e.g., based on metal oxide semiconductors MOX, may be applied to detection of target gases through redox reactions between the target gases and the oxide surface 128a of the layer of MOX sensing material 128. Sensing the target gas may occur at high temperatures, as previously discussed, and may include two steps: (1) redox reactions, during which oxygen ions O−, adsorbed on the surface 128a of the layer of MOX sensing material 128, may react with molecules of target gases, leading to an electrical variation of the metal oxide surface 128a, and (2) a transduction of such variation into a variation of an electrical resistance of the layer of MOX sensing material 128.

In one or more embodiments, at the working temperatures, the resistance of the MOX sensing material 128 may vary depending on the presence and concentration of target gases: the electrodes 124 electrically connected to the layer of MOX sensing material 128 may be used to detect the resistance value. Therefore, the obtained electrical signal, possibly after calibration, may be indicative of a gas concentration insofar as the resistance value of the layer of MOX sensing material 128 may vary as a function of the gas concentration level in air (parts per million—ppm).

One or more embodiments may thus relate to a method of reducing power consumption of (e.g., MOX-based) gas sensors 12 comprising a micro-hot plate driven in pulsed mode, i.e., intermitted heating mode.

Figure 2:
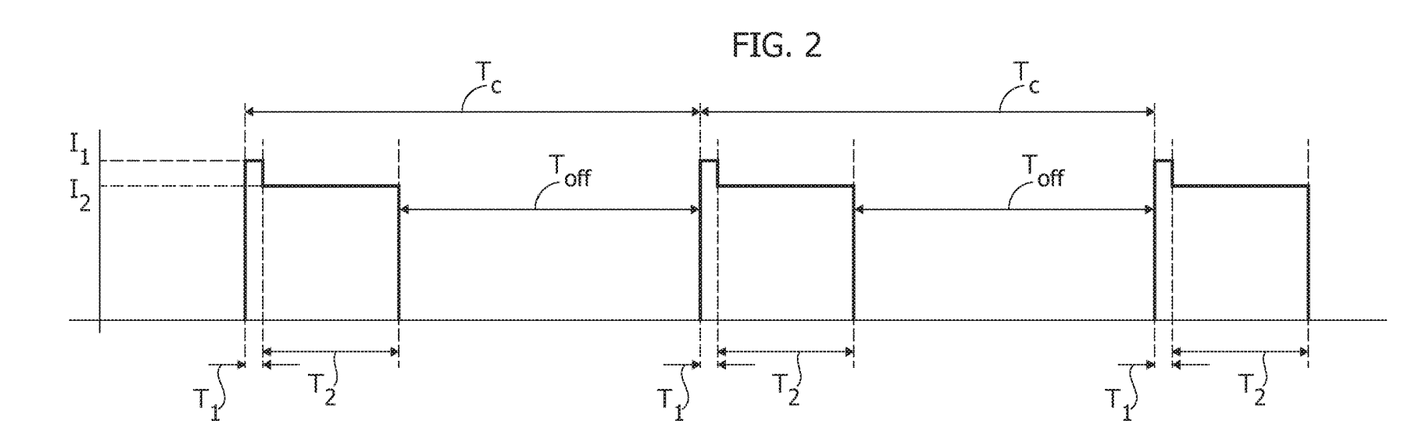
FIG. 2 represents a driving signal for the a MOX-based sensor.

FIG. 2 represents an example of a current signal over time that may be applied to the micro-hot plate for cyclically (e.g., a cycle may start every 60 s–Tc) activating (possibly rapidly) the sensor 12 by setting a first working temperature Temp1, by providing a first current I1 for a first time interval T1 (e.g., of about 0.5 s), and setting a second working temperature Temp2, by providing a first current I2 for a second time interval T2 (e.g., of about 4.5 s).

Also, an idle time interval Toff may be present in the driving cycle (e.g., of about 55 s), during which the current may be substantially null.

Figure 3:
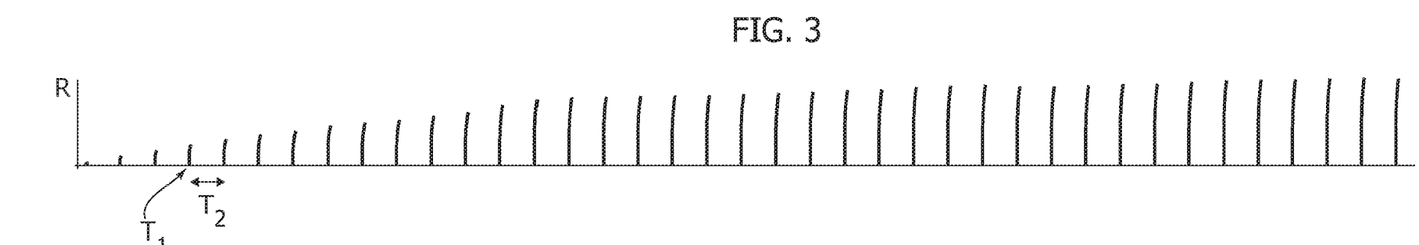
FIGS. 3 and 4 represent possible sensor responses to a driving signal such as the driving signal of FIG. 2.
Figure 4:
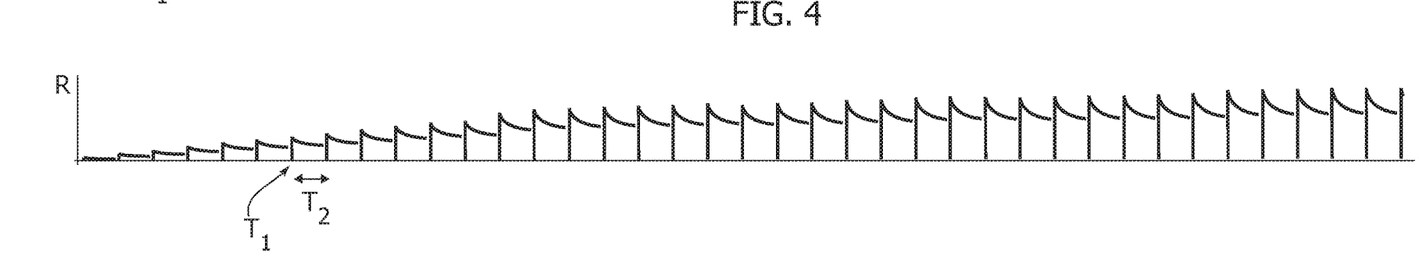

FIGS. 3 and 4 represent a possible non-limiting response R over time t of the sensor 12, e.g., a resistance response. The response R during the first time interval T1 and the second time interval T2 are illustrated, respectively. It will be observed that the response R during the idle time interval Toff is not visible in FIGS. 3 and 4.

The exemplified response R may occur under one or more circumstances:
during a target gas concentration variation: a low resp. high value of the resistance response R may correspond to a high resp. low gas concentration, and the transitory over time between the values may represent the variation over time of the gas concentration in air, and/or
during a warm-up transitory, following switch on of the gas sensor, the warm-up transitory may last tens of seconds up to several minutes, depending on heaters driving conditions.

In the following figures, parts or elements like parts or elements already discussed in connection with FIGS. 1 to 4 are indicated with like references and a corresponding detailed description will not repeated for the sake of brevity.

The sensor 12 may thus operate via intermitted heating, which may alternate powering the sensor 12 with a certain driving profile and discontinuing power. In the present non-limiting example, the cycle Tc may substantially correspond to 60 s, with an idle time interval Toff of about 55 s, and a driving profile that may last about 5 s. However, the values illustrated herein are merely preferred exemplary values, insofar as the driving profile may depend on sensor sensitivity, power consumption and/or slew rate of the sensor response to a target gas in the air.

Figure 5:
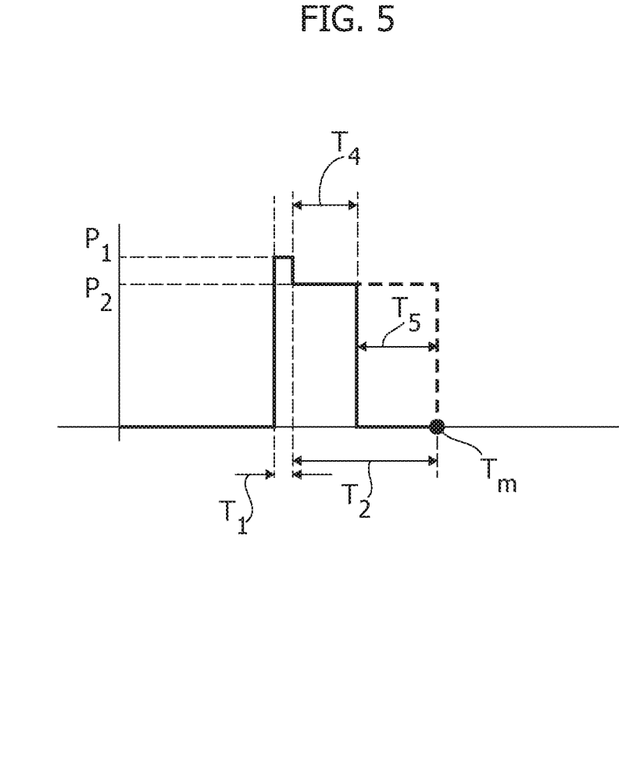
FIG. 5 represents a driving signal for a sensor according to one or more embodiments.

As illustrated in FIG. 5, the driving profile of the micro-hot plate MHP comprised in the sensor 12 may comprise:

providing a first power value P1 for the first time interval T1 (e.g., 0.5 s), providing a second power value P2 for a fourth time interval T4 (e.g., 2 s), wherein the fourth time interval T4 may be smaller than the second time interval T2, and discontinuing power for a fifth time interval T5, wherein the fifth time interval T5 may be substantially the difference between the second time interval T2 and the fourth time interval T4 (e.g., 2.5 s).

The second power value P2 may be different from the first power value P1, i.e., the second power value P2 may be lower (P2<P1) or higher (P2>P1) than the first power value P1, so that a predictable transitory phase may result which may be modelled via a predefined function.

Again, the idle time interval Toff may complete the cycle Tc, and may be interposed between two subsequent first time intervals T1. According to the previous driving profile, the time intervals during which the sensor 12 is powered (e.g., T1+T4) may be substantially smaller than the time intervals during which the power to the sensor 12 is discontinued (e.g., T5+Toff), e.g., time intervals during which the sensor 12 is powered may be lower than 5% of the entire cycle Tc.

Accordingly, in one or more embodiments, the fourth time interval T4 may be smaller than the second time interval T2, thereby reducing overall power consumption of the gas sensor.

However, in one or more embodiments, the possibility exists to predict values of the sensor response R during the fifth time interval T5. Accordingly, one or more embodiments may comprise extrapolating a value of the resistance R of the MOX sensing material 128 at a time Tm, corresponding to the end of the fifth time interval T5, i.e., the end of the second time interval T2 with respect to a conventional driving profile. The calculated value at instant Tm may be used for estimating a mean gas concentration at the end of the resistance response R transitory.

This may be done by calculating, during the fourth time interval T4, a prediction signal P, indicative of the behavior of the sensor response R during the fifth time interval T5, i.e., the time interval during which no power may be provided to the sensor 12 according to one or more embodiments (as opposed to conventional methods, wherein the micro-hot plate is powered to a second power value also during the fifth time interval T5).

The extrapolation of the predicted value at the time Tm, indicative of the resistance response R at the end of the fifth time interval T5, may comprise a first modeling, a second modeling and a reconstruction phase.

Figure 6:
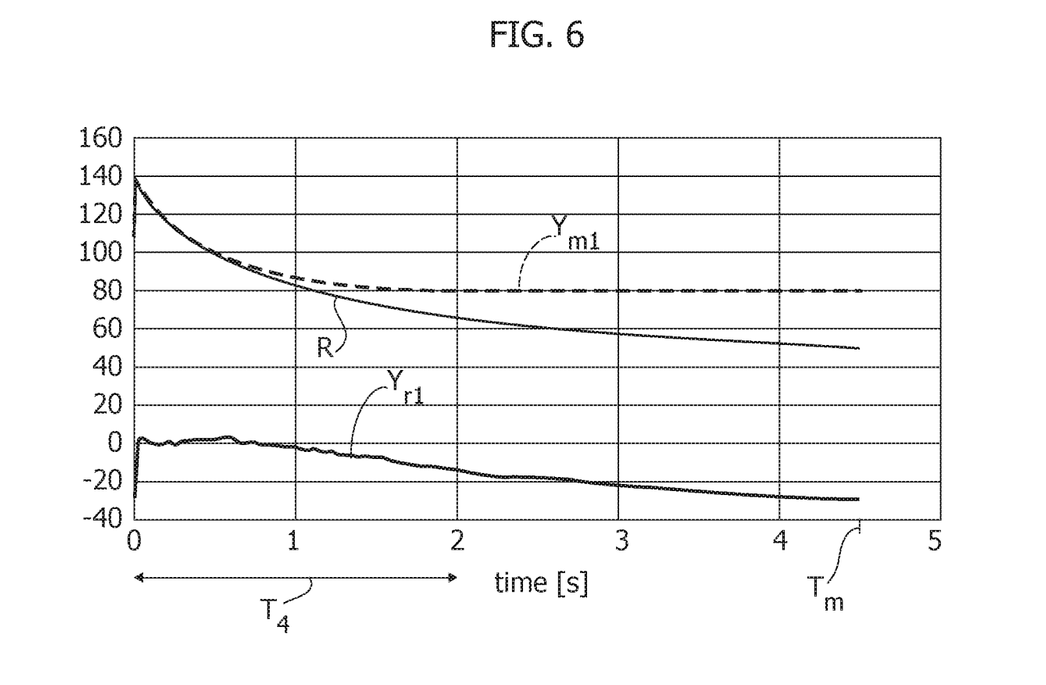
FIGS. 6 to 10 illustrate features of one or more embodiments.
Figure 7:
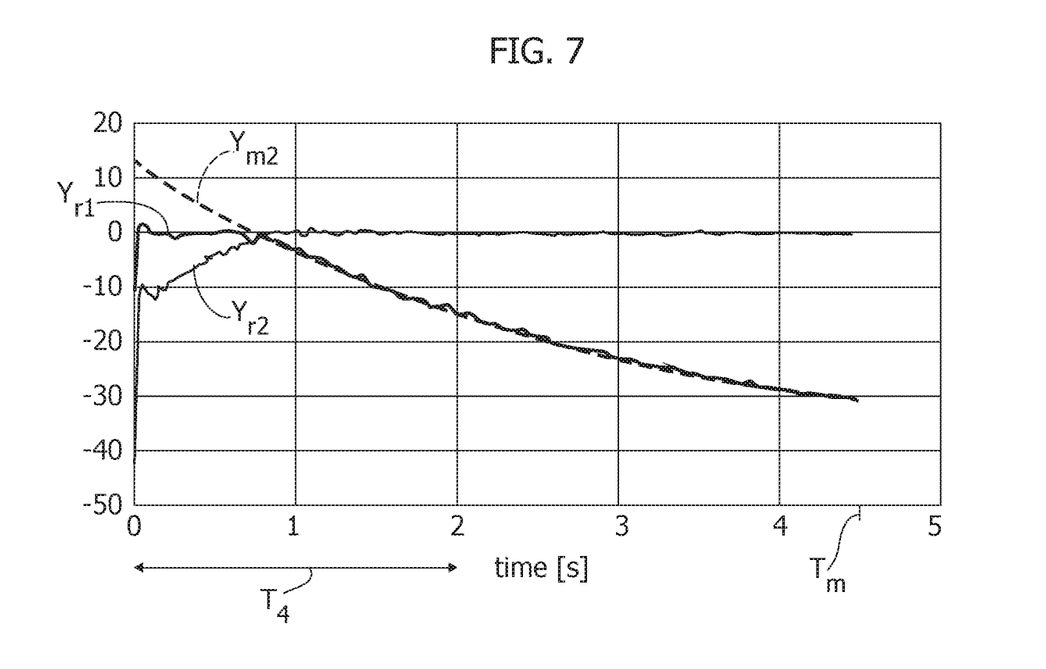
Figure 8:
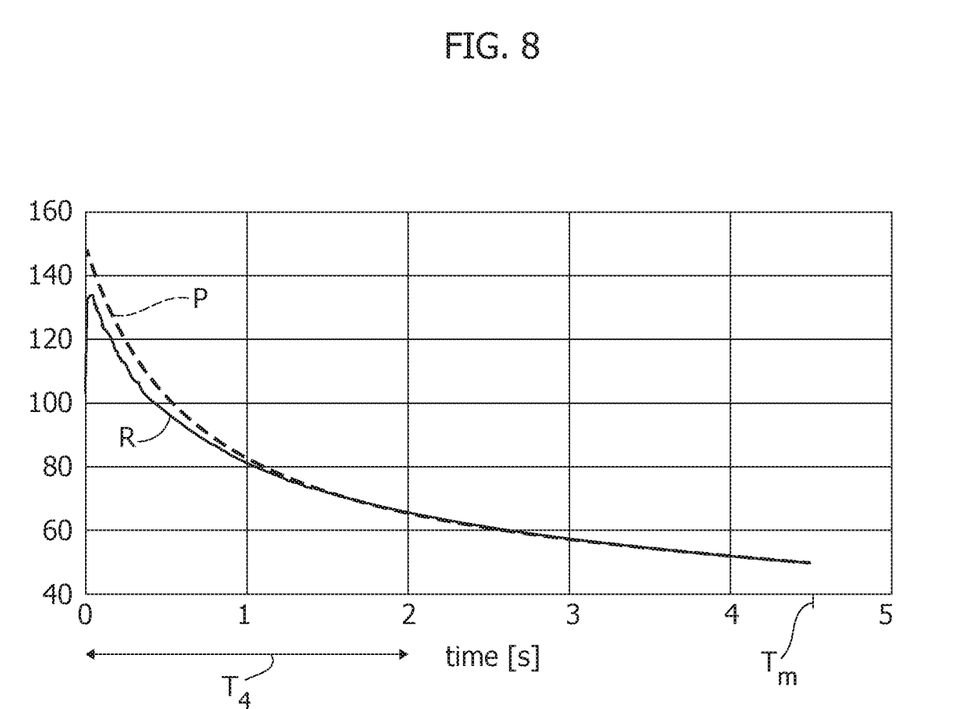

FIGS. 6 to 8 exemplify behaviors of the resistance response R over the second time interval T2, for a sensor driven with a conventional driving profile.

A prediction model may be calculated as a function of the sensor response R over the fourth time interval T4, being shorter than the second time interval T2 and starting at the start thereof (i.e., the first two seconds of the second time interval T2 in the present non-limiting example).

It will be appreciated that the instant 0 s represents the beginning of the second and fourth time interval T4 (corresponding to the end of the first time interval T1), the instant 2 s represents the end of the fourth time interval T4 and the instant 4.5 s represents the end Tm of the second time interval T2.

The first modeling phase, exemplified in FIG. 6, may comprise fitting to a first prediction model $Y_{m1}$, e.g., an exponential model, the resistance response R values collected, e.g., extracted, during a first sub-interval of the fourth time interval T4. The sub-interval may start at a first collection time within the fourth time interval T4 that may or may not coincide with the start thereof: for example, in the present example, the first sub-interval may comprise time instants 0.1 s to 0.6 s after the start of the fourth time interval T4). The first (exponential) model $Y_{m1}$ may comprise the equation:

$$Y_{m1}=a_0 e^{b_0 t}+c_0$$

wherein $a_0$, $b_0$ and $c_0$ may be calculated as a function of the response R, e.g., the MOX sensing material resistance response during the first sub-interval of the fourth time interval T4. In other words, the first prediction model $Y_{m1}$ may be calculated during the first sub-interval of the fourth time interval T4, and may vary as a function of the device and/or operation modes thereof.

The computed first model $Y_{m1}$ may represent the fast dynamics of the MOX gas sensor 12.

Also, in one or more embodiments, a first fit residue may be calculated as the difference between the sensor response R values (collected, e.g., extracted, during the entire fourth time interval T4 or a sub-interval thereof) and the first model values, $Y_{r1}=R-Y_{m1}$.

In one or more embodiments, a second modeling phase may be performed, exemplified in FIG. 7, comprising fitting to a second prediction model $Y_{m2}$, e.g., an exponential model, the first fit residue $Y_{r1}$ calculated during a second sub-interval of the fourth time interval T4. The second sub-interval may start at a second collection time within the fourth time interval T4 and may optionally end at a third collection time that may or may not coincide with the end of the fourth time interval T4: for example, in the present example, the second sub-interval may comprise time instants 1 s to 2 s after the start of the fourth time interval T4.

Also the second sub-interval of the fourth time interval T4 may vary as a function of the device and/or operation modes thereof. The second sub-interval of the fourth time interval T4 may be subsequent to the first sub-interval of the fourth time interval T4; also, the first and second sub-intervals may be partially superimposing, that is the second collection time may lie within the first sub-interval of the second time interval T4. The second (exponential) model $Y_{m2}$ may comprise the equation:

$$Y_{m2}=a_1 e^{b_1 t}+c_1$$

wherein $a_1$, $b_1$ and $c_1$ may be calculated as a function of the first fit residue $Y_{r2}$ during the second sub-interval of the fourth time interval T4. The computed second model $Y_{m2}$ may represent the slower dynamics of the MOX gas sensor 12.

In one or more embodiments, a second fit residue may be computed as $Y_{r2}=Y_{m2}-Y_{r1}$, the second fit residue being ideally null, and in a real scenario representing noise and/or negligible fluctuations of the response R.

One or more embodiments may therefore comprise calculating a prediction P of the response R of the sensor 12, e.g., the MOX sensing material resistance response of the MOX-based gas sensor, by summing (with sign) the first model $Y_{m1}$ and the second model $Y_{m2}$:

$$P=Y_{m2}+Y_{m1}.$$

Accordingly, one or more embodiments may allow calculation of a predicted value of the sensor resistance response R at the time Tm, corresponding to the end of the second time interval T2 and the end of the fifth time interval T5, at about 4.5 s in FIGS. 6 to 8.

In particular, in FIG. 8, the predicted values P during the entire second time interval T2 are represented, and the resistance response R of the gas sensor 12 driven with the driving profile exemplified in FIG. 2.

The prediction P and response R, at the time instant Tm, are substantially superimposing, the prediction being calculated using the response values received during the fourth time interval T4.

Figure 9:
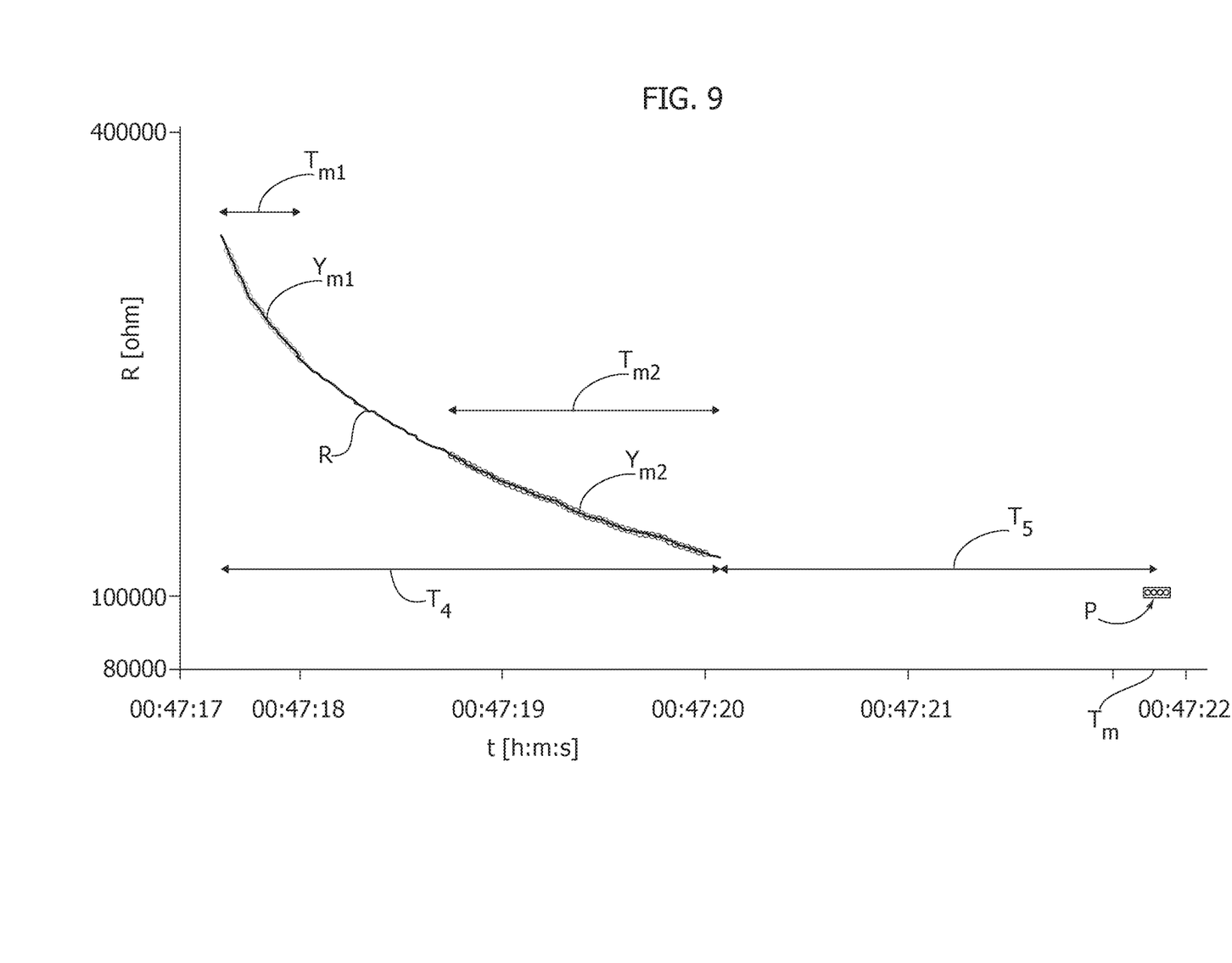

At the beginning of the prediction process, the prediction model is with two real poles; once the type of response R of the gas sensor is known (that may be e.g., a function of thermal and chemical processes), a model may be calculated by approximating the gas sensor to a second order dynamic system having real poles. If different sensors were employed, a different model may be exploited. FIG. 9 exemplifies a behavior over time of:

a set of response values R of a sensor driven with the driving profile of FIG. 5, a set of values of the first prediction model $Y_{m1}$ calculated for a first sub-interval $T_{m1}$ of the fourth time interval T4, a set of values of the second prediction model $Y_{m2}$, calculated for a second sub-interval $T_{m2}$ of the fourth time interval T4, the second sub-interval $T_{m2}$ being subsequent to and/or partially superimposing with the first sub-interval $T_{m1}$ and possibly ending at the end of the fourth time interval T4, and a set of predicted values P at about the time Tm, that may be indicative of the (MOX sensing material) resistance response R when the second power value P2 is provided to the MOX sensor 12 also during the fifth time interval T5.

It will be observed that only an example for the sake of brevity and understanding was provided herein. However, the method according to one or more embodiments should not be considered as limited to the exemplified fitting model: the solution according to one or more embodiments may be generalized to different current levels with different level variations during the duty cycle (i.e., on/off switching of the micro-hot plate). Therefore, one or more embodiments may relate to any duty cycle that may produce a predictable transitory phase in the sensor response R that may be fit on fly during the fourth time interval T4.

Figure 10:
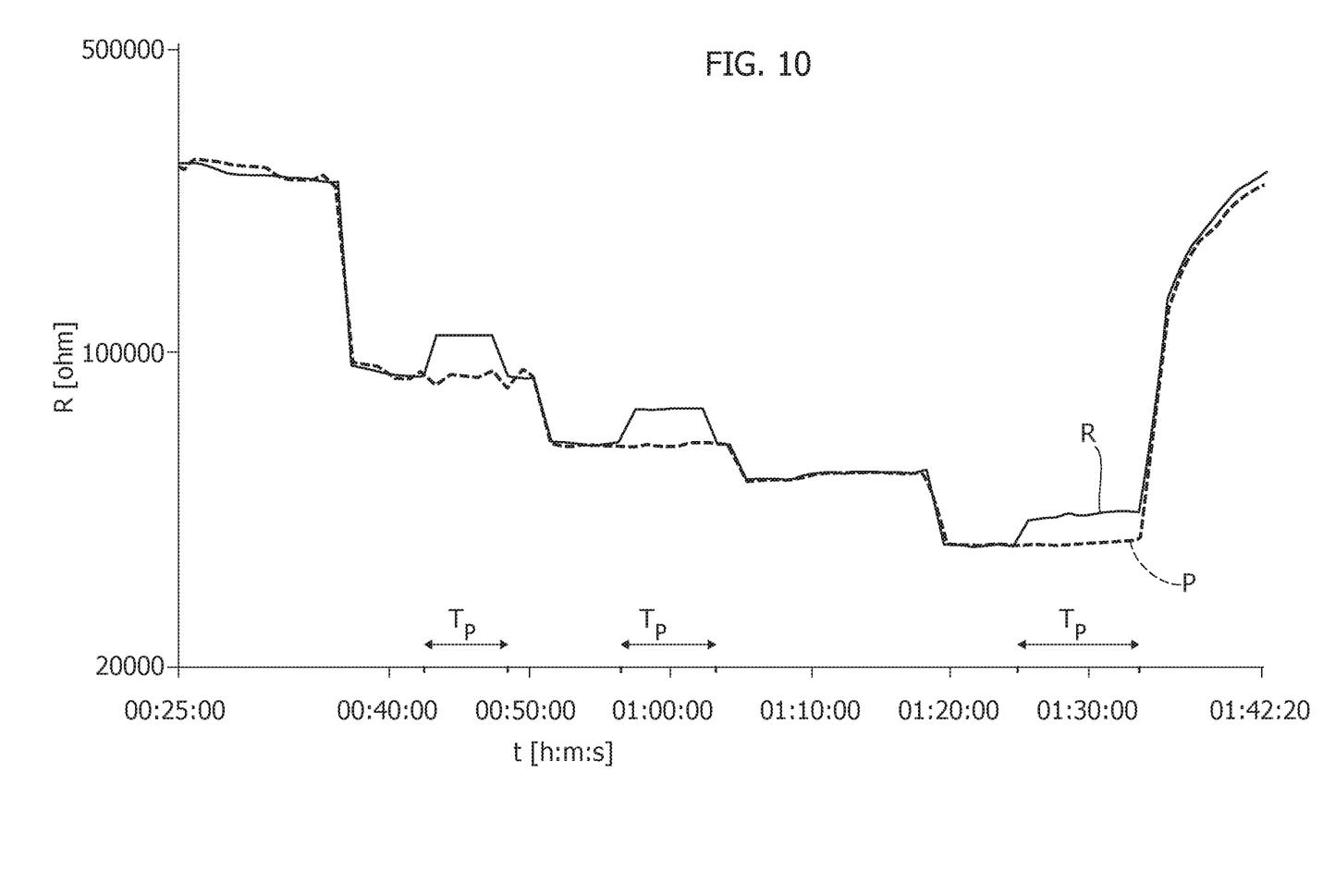

An example of analysis and prediction results may be observed in FIG. 10, wherein the represented values may be values acquired every cycle, at specific time instants thereof. As exemplified herein, if the cycle Tc substantially correspond to a minute, the values represented in FIG. 10 may be acquired each cycle, i.e., each minute, for example at the end of the fourth time interval T4 and/or at the end of the second time interval T2.

The gas concentration may be then calculated based on the predicted values P represented in FIG. 10, i.e., as a function of the response values R predicted at time instants Tm of each cycle.

In FIG. 10, the two curves may represent:

a curve—full line—representing the sensor response R, e.g., the MOX resistance value, of the sensor 12 at the end of the powered on interval of the gas sensor of each cycle Tc, that is the response values at the end of the second time interval T2 in case the sensor is driven with a conventional profile as exemplified in FIG. 2, or at the end of the fourth time interval T4 in case the sensor is driven with a reduced profile as exemplified in FIG. 5, a curve—dashed line—representing the prediction P of the sensor response at time instants Tm of each cycle Tc, i.e., at the end of the fifth time interval T5 of each cycle.

Four different VOC gas (e.g., ethanol) concentrations may be applied over time t to the gas sensor 12. The sensor response R and predicted values P may follow the variations in gas concentration: the variations of the response R and predicted values P may be exemplified by down steps.

The gas sensor 12 may be driven with a conventional profile, as exemplified in FIG. 2, or the gas sensor 12 may be driven with a profile according to one or more embodiments, as exemplified in FIG. 5, during time intervals $T_P$.

Accordingly, when the gas sensor 12 is driven with a conventional profile, the gas sensor 12 may be powered during the first and second time intervals T1+T2; the predicted value P may thus substantially correspond to the value that the response R exhibits. During time intervals $T_P$, the powering profile may be reduced, i.e., the gas sensor may be powered for the first and fourth time interval T1+T4: the predicted values P, i.e., values of the resistance calculated at instants Tm, do not correspond to the represented values of the resistance response R, which is switched off at the end of the fourth time interval T4: the values of the resistance responses R at the end of the fourth time interval T4 may be higher than the values at the end of the second time interval T2, due to the exponential behavior of the signal, as represented e.g., in FIGS. 6 to 8.

However, for each cycle, during time intervals Tp, even if the resistance response R may show a bias or error, the predicted value P (dashed line) may be correctly calculated and may produce a correct value of the gas concentration. In other words, even if the resistance response R, during time intervals Tp, may exhibit an offset due to the shorter driving profile with respect to the conventional driving profile, the predicted values P may still be used to calculate a correct gas concentration value.

It will be observed that one or more embodiments may facilitate achieving one or more of the following advantages:

the sensor, driven by the reduced pulsed profile, may provide a way of efficiently predicting the value of the resistance response R during operation, it may be possible to reduce power consumption of the sensor of about 40%, no degradation in performance of the sensor itself may be caused.

Figure 11:
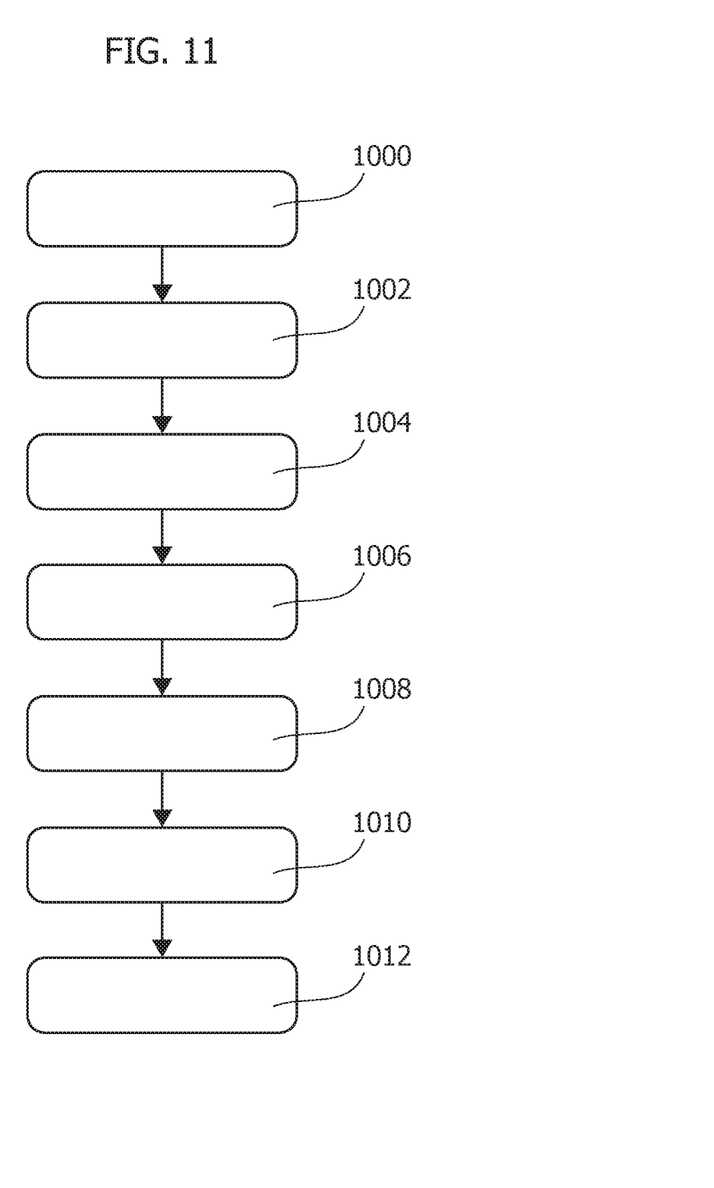
FIG. 11 illustrates a flow chart exemplifying a method according to one or more embodiments.

The method according to one or more embodiments may thus be exemplified in FIG. 11 and may comprise:

1000, providing the first power value P1 to the sensor 12 for the first time interval T1 (e.g., about 0.5 s), thereby obtaining a first working temperature T1 for the layer of metal oxide material 128, 1002, powering the second power value P2, different from the first power value P1, to the sensor 12 for the fourth time interval T4 (e.g., 2.0 s), thereby obtaining a temperature transient phase, between the first and the second working temperature for the layer of metal oxide material 128, during the second time interval T2 (i.e., the fourth time interval T4 plus the fifth time interval T5),

1004, collecting (MOX-based) sensor response, namely resistance values R, over the fourth time interval T4 (e.g., about 2 s),

1006, fitting the MOX sensing material response R to a first prediction model $Y_{m1}$, e.g., an exponential model, during a first sub-interval of the fourth time interval, plus calculating, during a second sub-interval of the fourth time interval T4, a first residue $Y_{r1}$ as the difference between the response R and the first prediction model $Y_{m1}$,

1008, fitting the first residue $Y_{r1}$ to a second prediction model $Y_{m2}$, e.g., an exponential model during the second sub-interval of the fourth time interval T4 which may be subsequent to and/or partially superimposing with the first sub-interval of the fourth time interval T4,

1010, reconstructing the prediction P as a sum (with sign) of the first prediction model $Y_{m1}$ and the second prediction model $Y_{m2}$, and

1012, predicting the MOX sensing material response R at the end of the second time interval T2, by extracting the prediction P indicative of the sensor response R, at the time Tm, corresponding to the end of the second time interval T2 (e.g., at about 5 s).

One or more embodiments may thus relate to a method which may comprise:

providing a sensor (e.g., 12) producing a sensing signal (e.g., R) which may be indicative of sensed entity—for example a gas concentration in air, powering the sensor, wherein the powering may comprise:

providing (e.g., 1000) a first power value (e.g., P1) for a first time interval (e.g., T1), providing (e.g., 1002) a second power value (e.g., P2) for a second time interval (e.g., T4), the second power value being different from the first power value, discontinuing powering for a third time interval (e.g., T5), collecting (e.g., 1004) from the sensing signal received from the sensor over the second time interval a first set of sensing values and a second set of sensing values, predicting (e.g., 1006 to 1012) a third set of values for the sensing signal over the third time interval as a function of the first set of sensing values and the second set of sensing values.

In one or more embodiments, predicting a third set of values for the sensing signal over the third time interval may comprise:

calculating (e.g., 1006) a first prediction model (e.g., $y_{m1}$) for the sensing signal by curve fitting the first prediction model with at least the first set of sensing values received over the second time interval (e.g., T4), calculating (e.g., 1006) a difference (e.g., $y_{r1}$) between the first prediction model and at least the second set of sensing values received over the second time interval (e.g., T4), calculating (e.g., 1008) a second prediction model (e.g., $y_{m2}$) for the sensing signal by curve fitting the second prediction model with the difference (e.g., $y_{r1}$) calculated over at least the second set of sensing values received over the second time interval, and calculating (e.g., 1010) a sum (e.g., P)—with sign, depending in turn on the sign of the difference $y_{r1}$—of the first prediction model and the second prediction model, the sum providing (e.g., 1012) a predicted third set of values for the sensing signal over the third time interval.

In one or more embodiments, the first prediction model and the second prediction model may comprise exponential models.

One or more embodiments may comprise cyclically repeating sequences of powering the sensor, receiving the sensing signal and predicting.

One or more embodiments may further comprise interleaving the cyclically repeated sequences with sensor idle time intervals (e.g., Toff), which may be substantially longer than (e.g., about at least ten times a sum of) the first, second and third time intervals.

In one or more embodiments the second time interval may be of equal or longer duration than the first time interval, and/or the first power value may be higher than the second power value, and/or the difference between the first and the second power values may be selectively controllable (i.e., it may be possible to provide power values that may produce a predictable behavior in the sensor response R), and/or the first time interval may precede the second time interval.

One or more embodiments may further comprise:

collecting the first set of sensing values over a first sub-interval (e.g., $T_{m1}$) of the second time interval starting from a first collection time, collecting the second set of sensing values over a second sub-interval (e.g., $T_{m2}$) of the second time interval starting from a second collection time.

The second collection time may be subsequent to the first collection time. Also, the second collection time may lie within the first sub-interval of the second time interval.

One or more embodiments may relate to a circuit (e.g., 10) which may comprise:

at least one input/output node (e.g., 22) for a sensing signal (e.g., R) indicative of sensed entity produced by a sensor (e.g., 12), at least one power node (e.g., 20) configured to power the sensor, a processor (e.g., 14), coupled with the at least one input/output node and the at least one power node, the processor may be configured to perform the acts of powering the sensor, receiving the sensing signal and predicting the third set of values according with the method of one or more embodiments.

Also, one or more embodiments may relate to a device (e.g., 1), which may comprise at least one sensor (e.g., 12) producing a sensing signal (e.g., R) indicative of sensed entity and a circuit (e.g., 11) according to one or more embodiments. The circuit may be arranged with the at least one input/output node coupled to the sensor to receive the sensing signal therefrom, and the at least one power node coupled to the sensor for powering the sensor.

In one or more embodiments, the sensor(s) may comprise a gas sensor, preferably a metal oxide semiconductor gas sensor.

Without prejudice to the underlying principles, the details and embodiments may vary, even significantly, with respect to what has been disclosed by way of example only, without departing from the extent of protection.

The extent of protection is defined by the annexed claims.

What is claimed is:

1. A method, comprising:

powering a sensor that produces a sensing signal indicative of a sensed entity, wherein the powering comprises:

providing a first power value for a first time interval;

providing a second power value for a second time interval, the second power value being different from the first power value;
discontinuing powering for a third time interval;
collecting a first set of sensing values and a second set of sensing values from the sensing signal received from the sensor over the second time interval; and
predicting a third set of values for the sensing signal over the third time interval as a function of the first set of sensing values and the second set of sensing values.

2. The method according to claim 1, wherein predicting the third set of comprises:
calculating a first prediction model for the sensing signal by curve fitting the first prediction model with the first set of sensing values received over the second time interval;
calculating a difference between the first prediction model and at least the second set of sensing values received over the second time interval;
calculating a second prediction model for the sensing signal by curve fitting the second prediction model with the difference calculated over at least the second set of sensing values received over the second time interval; and
calculating a sum of the first prediction model and the second prediction model, the sum providing a predicted third set of values for the sensing signal over the third time interval.

3. The method of claim 2, wherein the first prediction model and the second prediction model comprise exponential models.

4. The method of claim 1, comprising cyclically repeating sequences of powering the sensor, collecting the first and second sets of sensing values, and predicting the third set of values.

5. The method of claim 4, comprising interleaving the cyclically repeated sequences with sensor idle time intervals, the idle time intervals being substantially longer than the first, second and third time intervals.

6. The method of claim 1, wherein the second time interval is of equal or longer duration than the first time interval.

7. The method of claim 1, wherein the first power value is higher than the second power value.

8. The method of claim 1, wherein the difference between the first and the second power values is selectively controllable.

9. The method of claim 1, wherein the first time interval precedes the second time interval.

10. The method of claim 1, comprising:
collecting the first set of sensing values over a first sub-interval of the second time interval starting from a first collection time; and
collecting the second set of sensing values over a second sub-interval of the second time interval starting from a second collection time, wherein the second collection time is subsequent to the first collection time.

11. The method of claim 10, wherein the second collection time lies within the first sub-interval of the second time interval.

12. A device, comprising:
an input/output node configured to receive a sensing signal indicative of sensed entity produced by a sensor;
a power node configured to power the sensor; and
a processor functionally coupled to the input/output node and the power node, the processor configured to
provide a first power value for a first time interval;
provide a second power value for a second time interval, the second power value being different from the first power value;
discontinue powering for a third time interval;
collect a first set of sensing values and a second set of sensing values from the sensing signal received from the sensor over the second time interval; and
predict a third set of values for the sensing signal over the third time interval as a function of the first set of sensing values and the second set of sensing values.

13. The device of claim 12, wherein the processor is configured to predict the third by:
calculating a first prediction model for the sensing signal by curve fitting the first prediction model with the first set of sensing values received over the second time interval, wherein the first prediction model comprises an exponential model;
calculating a difference between the first prediction model and at least the second set of sensing values received over the second time interval;
calculating a second prediction model for the sensing signal by curve fitting the second prediction model with the difference calculated over at least the second set of sensing values received over the second time interval, wherein the second prediction model comprises an exponential model; and
calculating a sum of the first prediction model and the second prediction model, the sum providing a predicted third set of values for the sensing signal over the third time interval.

14. The device of claim 12, wherein the processor is configured to cyclically repeat sequences of powering the sensor, collecting the first and second sets of sensing values, and predicting the third set of values.

15. The device of claim 12, further comprising a sensor coupled to the input/output node and configured to provide the sensing signal indicative of sensed entity.

16. The device of claim 15, wherein the sensor is a gas sensor.

17. The device of claim 16, wherein the sensor is a metal oxide (MOX) gas sensor.

18. A portable device comprising:
a sensor package;
a metal oxide gas sensor disposed within the sensor package; and
an integrated circuit disposed within the sensor package and spaced from but electrically coupled to the metal oxide gas sensor, the integrated circuit comprising sensor circuitry configured to operate the sensor and a processor coupled to the sensor circuitry, the processor configured to
provide a first power value for a first time interval;
provide a second power value for a second time interval, the second power value being different from the first power value;
discontinue powering for a third time interval;
collect a first set of sensing values and a second set of sensing values from a sensing signal received from the sensor over the second time interval; and
predict a third set of values for the sensing signal over the third time interval as a function of the first set of sensing values and the second set of sensing values.

19. The portable device of claim 18, where the sensor circuitry a clock, a reference current/voltage generator, a heater current driver, an analog-to-digital converter, a multiplexer, a heater analog front-end, a sense analog front-end, and a heater and humidity H/T sensor.

20. The portable device of claim 18, wherein the device is a wearable device.

\* \* \* \* \*